United States Patent [19]
Spetzler

[11] Patent Number: 5,954,723
[45] Date of Patent: *Sep. 21, 1999

[54] METHOD AND APPARATUS FOR SECURING A CRANIAL PLATE WITH PINS

[76] Inventor: Robert F. Spetzler, 6107 N. Palo Cristi, Paradise Valley, Ariz. 85253

[ * ] Notice: This patent is subject to a terminal disclaimer.

[21] Appl. No.: 08/824,252

[22] Filed: Mar. 25, 1997

Related U.S. Application Data

[63] Continuation-in-part of application No. 08/518,103, Aug. 22, 1995, Pat. No. 5,669,912, which is a continuation of application No. 08/233,851, Apr. 26, 1994, Pat. No. 5,501,685.

[51] Int. Cl.⁶ .................................................. A61B 17/58
[52] U.S. Cl. ................................................ 606/72; 606/69
[58] Field of Search ................... 606/60, 61, 65, 606/67, 69, 72, 73, 86, 70; 411/388, 389, 458, 460, 487, 493–499

[56] References Cited

U.S. PATENT DOCUMENTS

| | | | |
|---|---|---|---|
| 4,157,674 | 6/1979 | Carlson et al. | 88/1 |
| 4,334,815 | 6/1982 | Knohl | 411/368 |
| 5,154,610 | 10/1992 | Gregorio Gracia | 433/74 |
| 5,613,968 | 3/1997 | Lin | 606/61 |

*Primary Examiner*—Michael Buiz
*Assistant Examiner*—Daphna Shai
*Attorney, Agent, or Firm*—Cahill, Sutton & Thomas

[57] ABSTRACT

A device for securing a previously removed cranial plate in position in a cranium to prevent relative movement between opposing bone edges includes a pin containing distal and proximal shanks having ends tapering to a relatively sharp point. One of the shanks is threaded for threadedly engaging the edge of either the cranial plate or the cranium. The shanks are arranged preferably symmetrically about a central collar which has a dimension transverse to the longitudinal axis of the shanks greater than the diameters of the shanks so that the collar forms distal and proximal opposing shoulders for limiting the insertion depth of the pin. A nut is located adjacent the collar or formed as part of the perimeter of the collar to facilitate rotation of the pin to screw in the threaded shank.

3 Claims, 4 Drawing Sheets

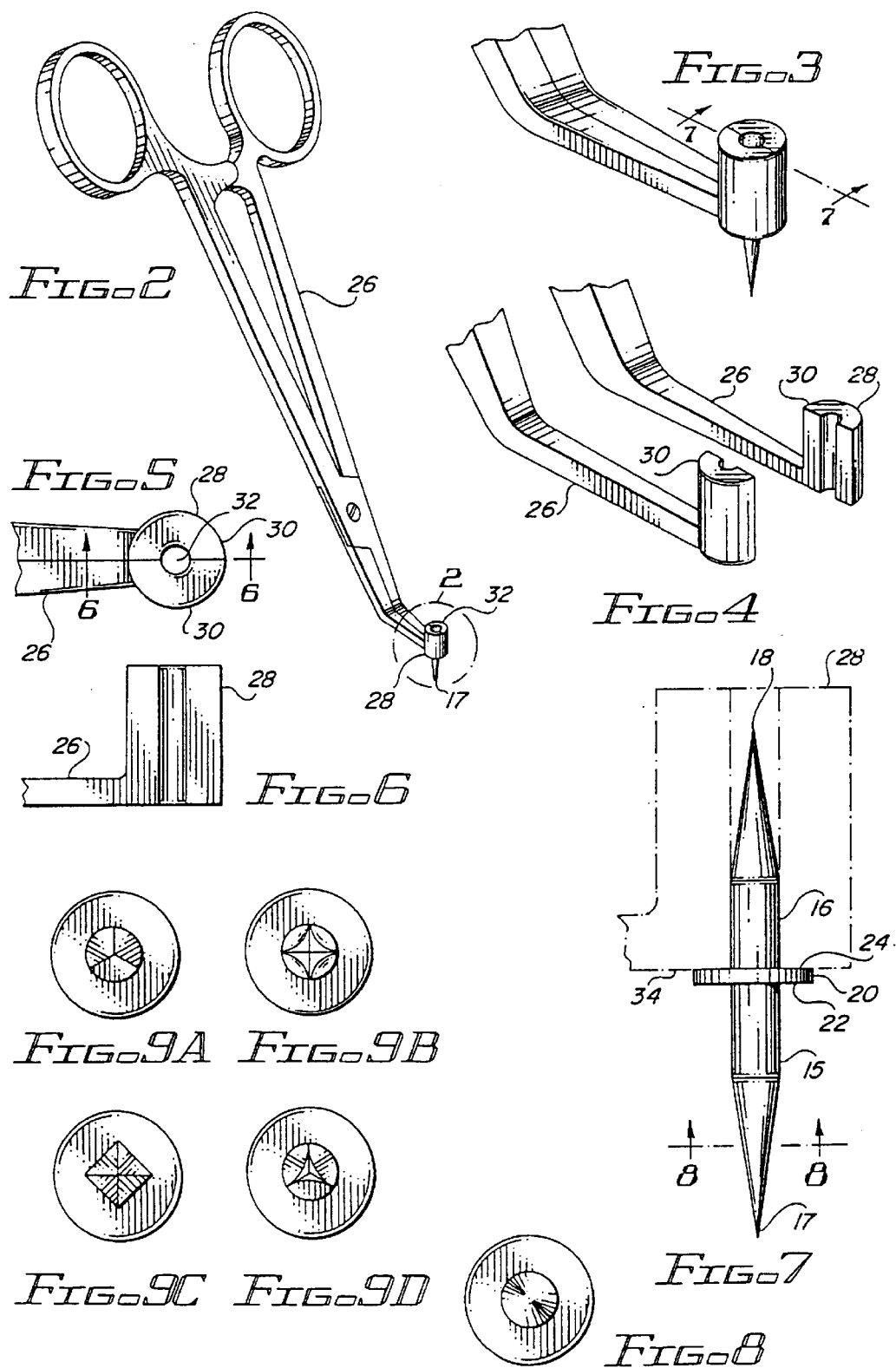

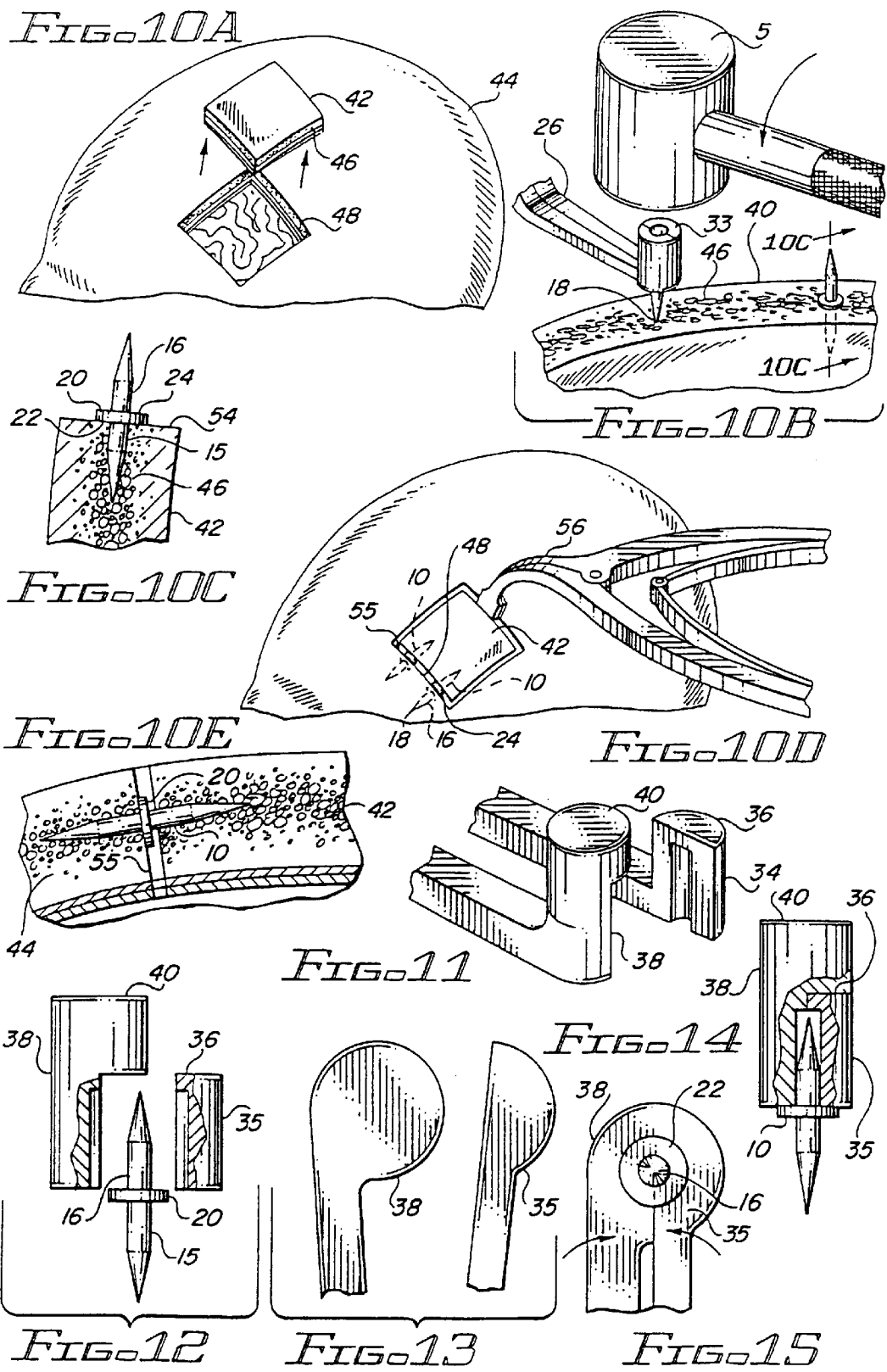

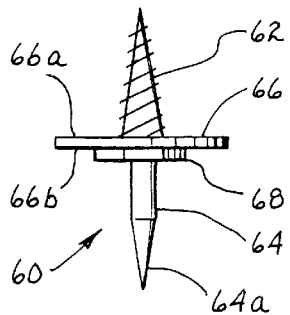 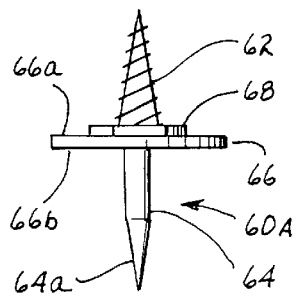 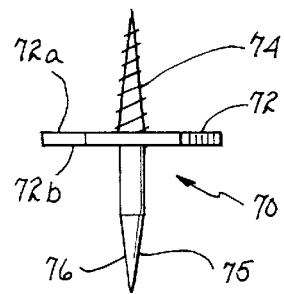
FIG. 16    FIG. 19    FIG. 22
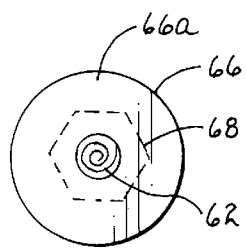 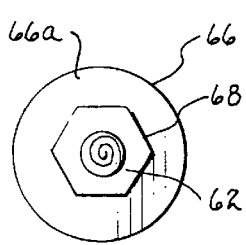 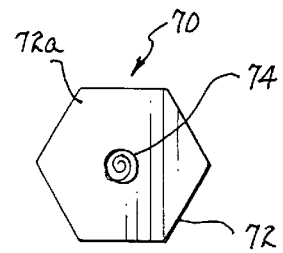
FIG. 17    FIG. 20    FIG. 23
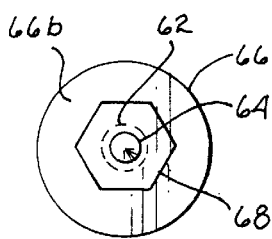 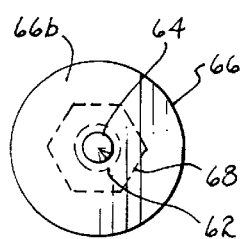 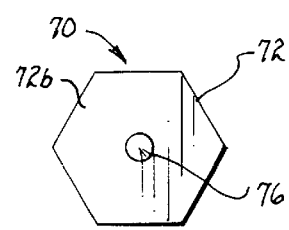
FIG. 18    FIG. 21    FIG. 24
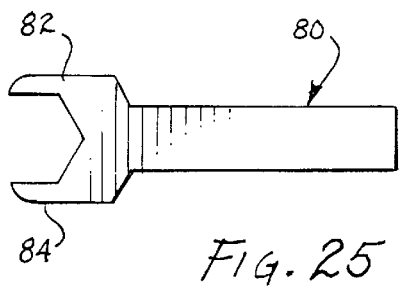
FIG. 25

METHOD AND APPARATUS FOR SECURING A CRANIAL PLATE WITH PINS

CROSS-REFERENCE TO RELATED APPLICATIONS

This application is a continuation-in-part of an application entitled "APPARATUS FOR SECURING A CRANIAL PIECE IN POSITION", Ser. No. 08/518,103, filed Aug. 22, 1995, now U.S. Pat. No. 5,669,912, and which application is a continuation of application entitled "METHOD FOR SECURING A CRANIAL PIECE IN POSITION", Ser. No. 08/233,851, filed Apr. 26, 1994, now U.S. Pat. No. 5,501,685, and issued Mar. 26, 1996.

BACKGROUND OF THE INVENTION

This invention relates to a method and apparatus for replacing and securing a cranial plate in position to prevent it from shifting from adjacent bone edges during the process of knitting or healing.

Various surgical procedures require the temporary removal of a cranial plate to permit access to strategic areas of the brain. In order for the cranial plate and cranium to fully knit together and heal following such surgical procedures, the cranial plate must be accurately positioned and secured back in place and all relative movement between opposing bone edges prevented during mending.

Although there are several devices used to rejoin bones other than the cranium, see for example U.S. Pat. Nos. 2,672,861, 4,516,569, 4,858,601 and 4,858,603, none of the devices disclosed in the above-listed patents are adaptable to the relatively thin flat structure of cranial bone. Furthermore, the forces acting on the bones for which the above-described patented devices are intended are quite different from the forces tending to shift cranial plates out of position in the cranium.

An important disadvantage of prior art technologies and devices is the likelihood of disfigurement. The removed cranial plate frequently extends below the hairline, thus rendering scars visible; the use of prior art screw techniques or metal staples can result in aesthetically unacceptable scar tissue plainly visible on the patient's forehead.

In view of the foregoing, it is therefore an object of the invention to provide a permanent, non-disfiguring apparatus for securing a previously removed cranial plate in position in a cranium to prevent relative movement between opposing bone edges.

A further object of the invention is to provide a method for replacing and securing a cranial plate in position in a cranial opening.

A still further object of the invention is to provide a kit for securing a previously removed cranial plate in position in a cranium to prevent relative movement between opposing bone edges.

SUMMARY OF THE INVENTION

The invention achieves the foregoing objects in one embodiment through the use of a pin adapted to secure a previously removed cranial plate in position in a cranial opening to prevent relative movement between opposing bone edges of the plate and opening. The pin comprises distal and proximal shanks having ends tapering to a relatively sharp point. One of the distal and proximal shanks is threaded to permit threaded engagement with the respective one of the cranium and the cranial plate. The shanks are arranged preferably symmetrically about a central collar which has a dimension transverse to the longitudinal axis of the shanks diameter greater than the diameters of the shanks so that the collar forms distal and proximal opposing shoulders for limiting the insertion depth of the shanks of the pin.

In a second embodiment, a method is provided for replacing and securing a cranial plate in position in a cranial opening. A surgical pin is positioned over a medullar portion of the cranial plate. The pin includes a threaded tapered distal shank and a proximal shank having an end tapering to a relatively sharp point. The shanks are arranged preferably symmetrically about a central collar which has a dimension transverse to the longitudinal axis of the shanks greater than the diameters of the shanks so that the collar forms distal and proximal opposing shoulders for limiting the insertion depth of the pin. A nut is formed adjacent the collar or as part of the perimeter of the collar. The distal threaded tapered shank of the pin is threadedly screwed into the medullar portion of the cranial plate so that the distal collar shoulder rests against the medullar portion of the cranial plate. The proximal tapered shank of the pin is inserted into a medullar portion of the opposing cranium so that the proximal collar shoulder rests against the medullar portion of the cranium. Alternatively, the proximal shank may be threaded and screwed into the medullar portion of the cranium prior to insertion of the distal shank into the medullar portion of the cranial plate.

In a third embodiment of the present invention, a kit is provided for securing a previously removed cranial plate in position in a cranium to prevent relative movement between opposing bone edges. The kit includes a surgical pin comprising distal and proximal shanks having ends tapering to a relatively sharp point. One of the distal and proximal shanks is threaded to permit threaded engagement with the respective one of the cranium and the cranial plate. The shanks are arranged preferably symmetrically about a central collar which has a dimension transverse to the longitudinal axis of the shanks greater than the diameters of the shanks so that the collar forms distal and proximal opposing shoulders for limiting the insertion depth of the pin. A nut is formed adjacent the collar or as part of the perimeter of the collar. The kit further includes a wrench having an end for turning the nut to threadedly engage the pin.

BRIEF DESCRIPTION OF THE DRAWINGS

FIG. 2 illustrates a forceps constructed in accordance with a preferred embodiment of the invention.

FIG. 3 is a more detailed illustration of the distal end of the forceps in a closed position, gripping a surgical pin.

FIG. 4 illustrates the distal end of the forceps in an open position.

FIG. 5 is a top view of the distal end of the forceps illustrated in FIGS. 2–4.

FIG. 6 is a sectional view of the distal end of the forceps shown in FIG. 5, taken on lines 6—6 of FIG. 5.

FIG. 7 is a side view of the distal end of the forceps gripping a surgical pin, as shown in FIG. 3, taken on line 7—7 of FIG. 3.

FIG. 8 is a top view of the distal end of the surgical pin shown in FIG. 7, taken on lines 8—8 of FIG. 7.

FIGS. 9A, 9B, 9C, and 9D illustrate top views of four alternative embodiments of the distal and proximal shanks of the surgical pin.

FIGS. 10A–10E illustrate a preferred embodiment of the method of the present invention.

FIGS. 11–15 illustrate a second embodiment of the distal end of the forceps.

FIG. 16 illustrates a side view of a variant pin.

FIG. 17 illustrates a top view of the variant pin shown in FIG. 16.

FIG. 18 illustrates a bottom view of the variant pin shown in FIG. 16.

FIG. 19 illustrates a further variant pin.

FIG. 20 illustrates a top view of the pin shown in FIG. 19.

FIG. 21 illustrates a bottom view of the pin shown in FIG. 19.

FIG. 22 illustrates a yet further variant of the pin.

FIG. 23 illustrates a top view of the pin shown in FIG. 22.

FIG. 24 illustrates a bottom view of the pin shown in FIG. 22.

FIG. 25 illustrates a representative wrench useable with any of the pins shown in FIGS. 16, 19, and 22.

DESCRIPTION OF THE PREFERRED EMBODIMENTS

Figure 1A:
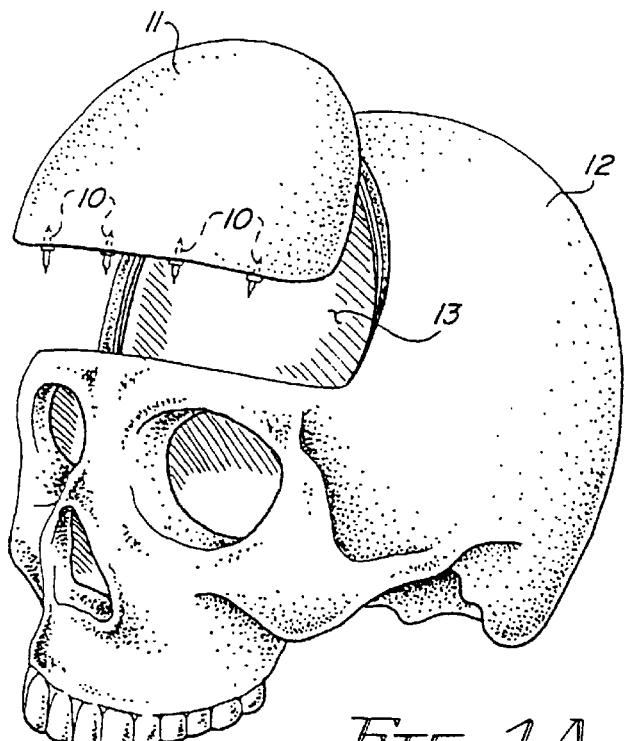
FIG. 1A illustrates a cranial plate removed from a cranium.

FIGS. 1–8 illustrate a first embodiment of an apparatus for securing a previously removed cranial plate in position in a cranial opening to prevent relative movement between opposing bone edges. A surgical pin is indicated generally by reference numeral 10; the surgical pin is constructed of suitable material such as titanium or surgical steel.

Figure 1B:
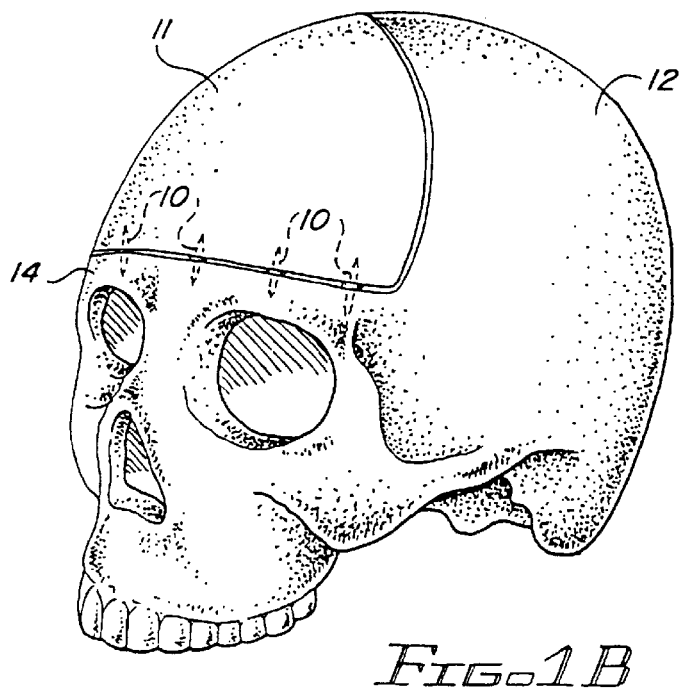
FIG. 1B illustrates the cranial plate of FIG. 9A secured in position in accordance with a preferred embodiment of the invention.

FIG. 1A illustrates a cranial plate 11 removed from a cranium 12, leaving a large cranial opening 13 extending into forehead 14. FIG. 1B illustrates cranial plate 11 of FIG. 1A secured in position in cranium 12 by means of a plurality of pins 10, in accordance with a first embodiment of the present invention.

Pin 10 includes a distal shank 15 and a proximal shank 16; the distal and proximal shanks each have an end, respectively indicated by reference numerals 17 and 18, which tapers to a relatively sharp point; preferably, the taper, expressed as the difference in diameter per millimeter of length, is in the range of from approximately 0.4 millimeter per millimeter of length, to approximately 0.2 millimeter per millimeter of length.

Distal and proximal shanks 15 and 16 are preferably cylindrical and of approximately equal lengths and diameters, as shown in FIG. 8. FIGS. 9A, 9B, 9C and 9D illustrate other acceptable cross-sectional shapes. Depending on the particular circumstances, one shank might have a greater diameter and/or length that the other shank.

Distal and proximal shanks 15 and 16 are arranged, preferably symmetrically, about a central collar 20. Central collar 20 has a dimension 21 transverse to the longitudinal axis of distal and proximal shanks 15 and 16 which dimension is greater than the diameters of the distal and proximal shanks, thereby forming distal and proximal opposing shoulders, respectively indicated by reference numerals 22 and 24, for limiting the insertion depth of pin 10.

Pin 10 can be made in a range of sizes depending on the patient and the particular application. The following dimensions are given for one size to indicate the proportions. Thus, for a typical size, distal and proximal shanks 15 and 16 are each approximately 3 millimeters long, and taper from a diameter of approximately 1 millimeter adjacent each respective shoulder 22 and 24, to a diameter of approximately 0.1 millimeter at the distal and tapered ends 17 and 18, respectively. Central collar 20 has a diameter of approximately 5 millimeters, and is approximately 0.75 millimeters thick.

Also illustrated in FIGS. 2–7 is a forceps 26 having a distal end 28 comprising a pair of opposing semicylindrical members 30. Forceps 26 has the following two functions: to provide means for gripping pin 10 to accurately position it, and to provide a striking surface for use in driving the pin into the proper place. Thus, when semicylindrical members 30 are closed together (as shown, for example, in FIGS. 2–3) they form a cylindrical chamber 32 adapted to grip proximal shank 16 of pin 10, and a striking surface 33. As is best illustrated in FIG. 7, when semicylindrical members 30 are closed together around pin proximal shank 16, proximal shoulder 24 rests against bottom end 34 of forceps distal end 28, and distal shank 15 protrudes therefrom; proximal tapered end 18 is enclosed within cylindrical chamber 32 beneath striking surface 33.

In the alternate embodiment illustrated in FIGS. 11–15, semicylindrical members 30 further include means for covering the top of cylindrical chamber 32 when the semicylindrical members are closed together, providing further protection for the sharp point of proximal tapered end 18. As illustrated in FIG. 11, first alternate semicylindrical member 35 includes a semicircular cap 36 and second alternate semicylindrical member 38 includes a circular cap 40. When first and second alternate semicylindrical members 35 and 38 are closed together as illustrated in FIGS. 13 and 14, semicircular cap 36 covers approximately half of the top of cylindrical chamber 32; circular cap 40 covers both the remaining half of the top of the cylindrical chamber and also the semicircular cap, and provides an alternative striving surface.

The method for replacing and securing a cranial plate 42 in position in a cranial opening 45 will now be described with reference to FIGS. 10A–10E. FIG. 10A illustrates a cranial plate 42 removed from its position in cranium 12, leaving a cranial opening 45. Both cranial plate 42 and cranium 12 contain soft interior marrow, or medullar, portions, referred to respectively by reference numerals 46 and 48.

FIG. 10B illustrates one step of the method of the present invention. The relatively sharp tapered end 17 of distal shank 15 is positioned over cranial plate medullar portion 46 by means of forceps 26; as explained earlier, the forceps include distal end 28 for gripping proximal shank 16 of pin 10. Distal shank 15 is inserted into medullar portion 46 by tapping striking surface 33 of forceps distal end 28 with a striking device such as hammer 52, thereby driving distal tapered end 17 and distal shank 15 into the medullar portion. As is illustrated in FIG. 10C, the depth of penetration of medullar portion 46 by pin 10 is limited by distal shoulder 22, which rests against outer edge 54 of the medullar portion after distal shank 15 has been fully inserted.

Next, as is illustrated in FIG. 10D, proximal shank 16 is inserted into adjacent bone edge 55 of cranium 44 by pushing the relatively sharp proximal tapered end 18 into the appropriate position in cranium medullar portion 48 by means of a tool such as spreader 56. Analogous to insertion of distal shank 15 in cranial plate 42, the depth of penetration of medullar portion 48 by proximal shank 16 is limited by proximal shoulder 24, which rests against outer edge 58 of cranial medullar portion 48 after proximal shank 16 has been fully inserted. As with FIGS. 1A and 1B, FIG. 10D illustrates the likely situation that a plurality of pins 10 will be necessary to secure a cranial plate in a cranium.

As is best illustrated in FIG. 10E, after cranial plate 42 is secured back in its correct position in cranium 44 by means of the present invention, the distance between the cranial plate and opposing cranium bone edge 55 will be the thickness of central collar 20 (approximately 0.75 millimeters), which thickness is kept to a minimum to allow optimal knitting to occur between the cranial plate and the opposing cranium bone edge, and to reduce formation of visible scar tissue.

Referring jointly to FIGS. 16, 17, and 18, there is shown a variant pin 60 useable as a substitute for pin 10 described above. Pin 60 includes a threaded shank 62, which may be constant diameter or tapered as shown, for threaded engagement with either medullar portion 46 of cranial plate 42 or medullar portion 48 of cranium 12. To facilitate threaded engagement, a nut 68 may be attached to or formed as a part of collar 66. As noted, nut 68 is on the side of collar 66 opposite from threaded shank 62. Such location permits the shoulder (66a or 66b) of collar 66 to be abutted adjacent the respective edge of the cranial plate or the cranium into which threaded shank 62 has been inserted. Tapered shank 64 extends axially from nut 68 for insertion into the other of the cranial plate or the cranium, as described above. Although tapered shank 64 is shown as having a cylindrical section terminated by a tapered end 64a, the pin may be tapered from its base to its point; either configuration may be referred to as a tapered shank.

Because nut 68 extends axially for a discrete distance from collar 66, the respective one of outer edge 54 of the medullar portion of the cranial plate or bone edge 55 of the cranium into which tapered shank 64 is inserted may be recessed sufficiently to receive the nut and thereby permit the shoulder (66a or 66b) of collar 66 to be placed against the respective outer edge or bone edge.

A further variant pin 60A is illustrated in FIGS. 19, 20, and 21. This variant includes nut 68 on the side (66a) of collar 66 opposite from tapered shank 64. Upon threaded engagement of threaded shank 62 with the medullar portion 46,48 of either cranial plate 42 or cranium 44, respectively, variant pin 60A is rotated until the nut abuts the respective edge. To permit abutment of the shoulder (66a or 66b) of collar 66, a depression may be formed in the edge to accommodate nut 68 along with the wrench or other tool used to rotate pin 60A.

Referring jointly to FIGS. 22, 23, and 24, there is illustrated a still further variant pin 70. Herein, collar 72 is formed as a hexagon readily and easily engageable by a suitably sized wrench or other tool. Alternatively, the surface of the perimeter of the collar may be serrated, cross-hatched, or otherwise made more grippable by a plier-like tool or a device to grip pin 70 and faciliate rotation. Upon threaded engagement of threaded shank 74 with medullar portion 46,48 of the cranial plate 42 or cranium 44, respectively, the shoulder (72a or 72b) of collar 72 will abut against the respective edge. Upon insertion of end 75 of tapered shank 76 into the other of the medullar portion of the cranial plate or the cranium, the shoulder (72a or 72b) of collar 72 will abut thereagainst. Accordingly, pin 70 embodies all of the essential benefits described above with respect to pin 10 and yet provides the additional capability for threadedly engaging either the cranial plate or the cranium.

A wrench 80 is illustrated in FIG. 25. This representative wrench includes jaws 82,84 for engaging and rotating either of nuts 68 shown with pin 60 and variant pin 60A or with collar 72 of variant pin 70 formed in the configuration of a nut. It is to be understood that the configuration of the nut may have an appropriate number of sides or facets or gripping surfaces commensurate with ease of performing the respective surgical procedure.

While the invention has been described with reference to preferred embodiments thereof, the description is for illustrative purposes only and is not to be construed as limiting the scope of the invention. Various modifications and changes may be made by those skilled in the art without departing from the true spirit of the scope of the invention as defined by the appended claims. For example, in the method of the present invention, for some patients it may be necessary to insert pin 10 first into cranium medullar portion 48, followed by insertion of proximal shank 16 into cranial plate medullar portion 46, rather than the opposite, as described above. In addition, although central collar 20 has been depicted as having a circular cross-section, which is preferred, virtually any cross-sectional shape will be suitable. The arrangement of distal and proximal shanks 15 and 16 on central collar 20 need not always be symmetrical, depending on the application.

I claim:

1. A surgical pin for securing a cranial plate in alignment with a cranium to prevent the cranial plate from shifting from adjacent bone edges during the process of knitting or healing, said pin comprising in combination:

distal and proximal shanks arranged about a central collar having a dimension transverse to the longitudinal axis of the shanks greater than the diameters of the shanks to form distal and proximal opposing shoulders for limiting the insertion depth of the pin into the medullar portion of the cranial bone, one of said shanks including threads for threadedly engaging the bone edge of the respective cranial plate or cranium, a nut formed integrally with said pin and located adjacent said collar for gripping said pin to rotate said pin about the longitudinal axis and engage said threads, the other of said shanks having a tapered unthreaded configuration terminating in a sharp point to facilitate insertion into said bone edges.

2. The surgical pin set forth in claim 1 wherein the distal and proximal shanks are of approximately equal length and diameter.

3. The surgical pin set forth in claim 1 wherein each of said distal and proximal shanks is tapered.

* * * * *